(12) United States Patent
Pessin (10) Patent No.: US 8,192,407 B2
(45) Date of Patent: Jun. 5, 2012

(54) SYRINGE NEEDLE PROTECTIVE DEVICE AND INJECTING DEVICE PROVIDED THEREWITH

(75) Inventor: Olivier Pessin, Grezieu la Varenne (FR)

(73) Assignee: Tech Group Europe Limited, Dublin (IE)

( * ) Notice: Subject to any disclaimer, the term of this patent is extended or adjusted under 35 U.S.C. 154(b) by 366 days.

(21) Appl. No.: 11/574,333

(22) PCT Filed: Jul. 28, 2005

(86) PCT No.: PCT/FR2005/001983
§ 371 (c)(1),
(2), (4) Date: May 2, 2007

(87) PCT Pub. No.: WO2006/027447
PCT Pub. Date: Mar. 16, 2006

(65) Prior Publication Data
US 2007/0270759 A1    Nov. 22, 2007

(30) Foreign Application Priority Data
Aug. 27, 2004 (FR) ...................................... 04 09163

(51) Int. Cl.
*A61M 5/32* (2006.01)
*A61M 5/00* (2006.01)

(52) U.S. Cl. ......................... 604/198; 604/192; 604/263

(58) Field of Classification Search .................. 604/192, 604/198, 164.08, 110, 181, 187, 193, 197, 604/263
See application file for complete search history.

(56) References Cited

U.S. PATENT DOCUMENTS

| | | | | |
|---|---|---|---|---|
| 5,141,500 A | * | 8/1992 | Hake | 604/198 |
| 5,201,720 A | * | 4/1993 | Borgia et al. | 604/198 |
| 5,591,138 A | | 1/1997 | Vaillancourt | |
| 5,817,064 A | * | 10/1998 | DeMarco et al. | 604/198 |
| 5,997,513 A | * | 12/1999 | Smith et al. | 604/198 |
| 6,013,059 A | * | 1/2000 | Jacobs | 604/198 |
| 6,086,566 A | * | 7/2000 | Arnissolle | 604/192 |
| 6,159,184 A | * | 12/2000 | Perez et al. | 604/192 |
| 6,997,901 B2 | * | 2/2006 | Popovsky | 604/110 |
| 2005/0020985 A1 | * | 1/2005 | Doyle | 604/192 |

FOREIGN PATENT DOCUMENTS

| | | |
|---|---|---|
| FR | 2835753 A1 | 8/2003 |
| FR | 2837107 A1 | 9/2003 |
| WO | WO 01/24856 A1 | 4/2001 |

* cited by examiner

*Primary Examiner* — Kevin C Sirmons
*Assistant Examiner* — Shefali Patel
(74) *Attorney, Agent, or Firm* — Panitch Schwarze Belisario & Nadel LLP (57) ABSTRACT

The inventive needle protective device (2) comprises a protective support (20), a movable needle protector (22), a compression spring (24) applied between the protective support (20) and the needle protector (22) and means (38, 40, 54) for initially holding the needle protector (22) oppositely to the compression spring (24) action, wherein said means (38, 40, 54) are releasable by the needle protector (22) displacement in a releasing direction with respect to the protective support (20). Said device also comprises mechanical means (45, 62) for locking the needle protector (22) actuatable by the action of a needle protective cap engaged into the end opening (60) of the needle protector (22) and deactivatable by the cap releasing.

6 Claims, 7 Drawing Sheets

SYRINGE NEEDLE PROTECTIVE DEVICE AND INJECTING DEVICE PROVIDED THEREWITH

The present application is the U.S. national stage application of International Application PCT/FR2005/001983, filed Jul. 28, 2005, which international application was published on Mar. 16, 2006, as International Publication WO/2006/027447. The International Application claims priority of French Patent Application 0409163, filed Aug. 27, 2004.

The present invention relates to a needle protection device comprising:
- a protector support delimiting a conduit for receiving a syringe body;
- a needle protector delimiting an end opening for the passage of the needle and a needle protection cap and having at its other end radial protuberances forming a finger rest, which needle protector is movable relative to the protector support between a retracted position and an extended position;
- a compression spring applied between the protector support and the needle protector; and
- means for the initial fixing of the needle protector counter to the action of the compressed spring, which means are releasable by displacement of the needle protector relative to the protector support in a releasing direction.

The invention concerns, in particular, the field of pre-filled disposable injection syringes intended, in particular, for intramuscular or subcutaneous injections.

These devices are intended to minimise the risk of the user being accidentally jabbed after the injection, since once the content of the syringe has been injected, the needle of the syringe is withdrawn from the patient and the protector is automatically brought into the extended position beyond the injecting end of the needle.

A protection device of this type is described, in particular, in document FR 2 837 107.

The device described in this document is such that the positioning of the needle protector is triggered by backward axial displacement of the protector relative to the needle support. This displacement is carried out counter to the spring interposed between the protector support and the protector, so the needle protector is fixed, to prevent triggering of the device, merely by the force of the spring.

The syringes positioned in protection devices of this type are initially equipped with a movable needle protection cap. The syringe thus equipped with the cap is introduced by the trailing or proximal end of the protector. Once the syringe has been positioned in the device, the cap is removed from the leading end opening in the protector.

The caps are generally made of rubber and are held at the end of the syringe around the needle by radial resilient action of the rubber. There can therefore be a relatively high degree of force fixing the cap at the end of the syringe body, thus necessitating the exertion of a strong pull on the protector to allow withdrawal thereof.

To hold the device during withdrawal of the cap, the user holds onto the protector from the radial protuberances which form a finger rest and are provided on the protector.

Thus, the exertion of a pull on the cap can drive the syringe and the protector support integral therewith and axially displace the protector relative to the protector support, and this then triggers the device even though the injection has not yet been performed.

The object of the invention is to propose a needle protection device with which the risks of accidental triggering during withdrawal of the needle protection cap are reduced.

The invention accordingly relates to a protection device of the aforementioned type, characterised in that it comprises mechanical means for locking the needle protector relative to the protector support in the releasing direction, which means are activated under the action of a needle protection cap engaged with the end opening in the needle protector and are deactivatable by releasing the needle protection cap outside the end opening in the needle protector.

According to further features of this device, taken in isolation or in any technically feasible combination:
- the mechanical locking means comprise at least a resiliently deformable tongue integral with a first of the protector and the support, the or each tongue being displaceable between a locking position, in axial abutment against the second of the protector and the support in the presence of the cap, and an unlocking position, remote from the second of the protector and the support in the absence of cap, the or each tongue extending, while at rest, into its unlocking position, and the or each tongue has an actuating range for the deformed holding thereof in the locking position under the action of the cap engaged with the end opening in the needle protector;
- the or each tongue has a projection capable of engaging in an orifice formed in the second of the protector and the support;
- the or each tongue is integral with the needle protector; and
- the or each tongue extends in the extension of the protector support at the front end thereof.

The invention further relates to an injection device comprising, on the one hand, a syringe comprising a tubular body, to the distal end of which a needle is fixed, and an injection piston mounted to slide in the body and, on the other hand, a needle protection device as described hereinbefore.

Figure 1:
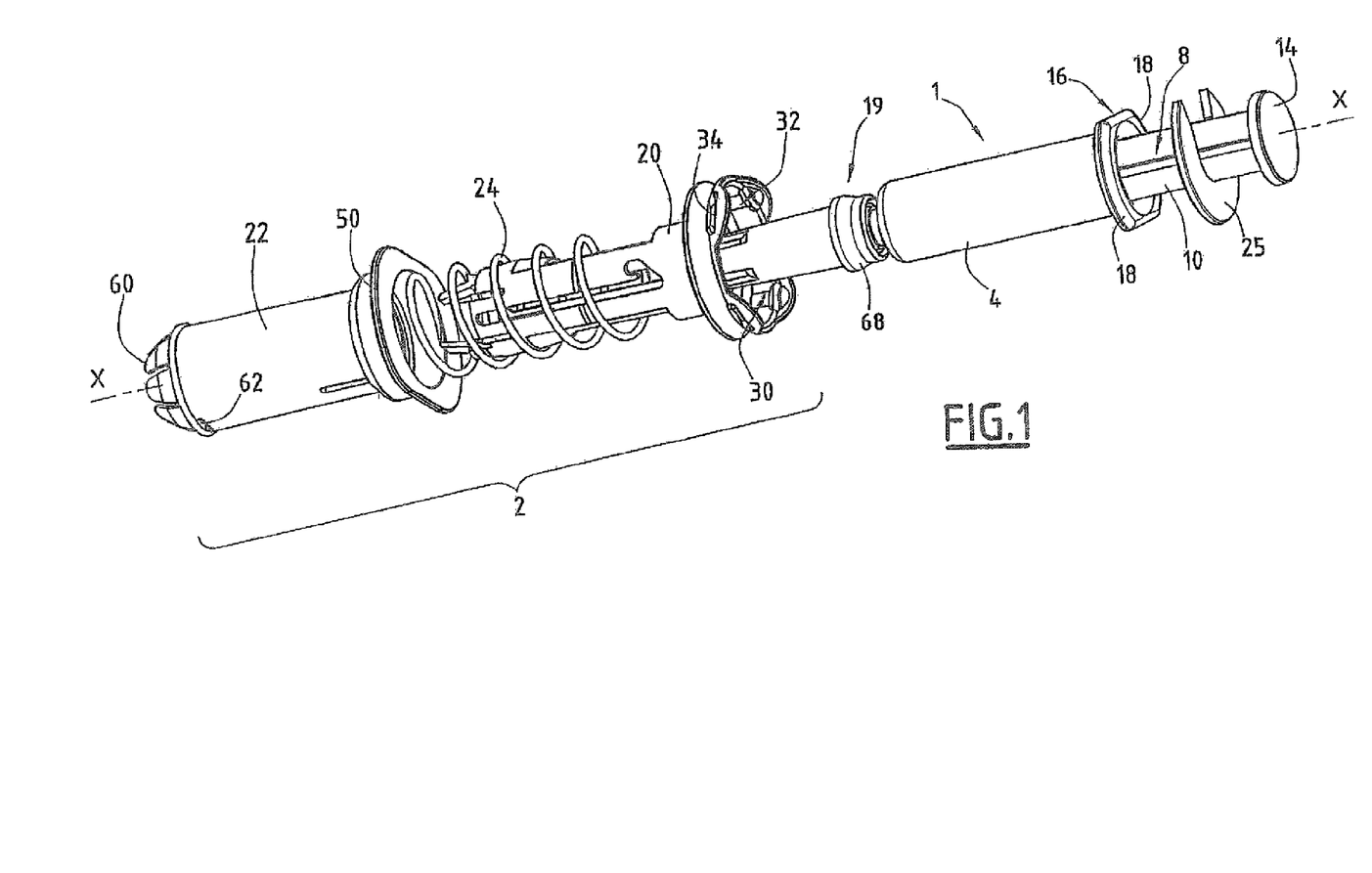
FIG. 1 is an exploded perspective view of an injection device according to the invention prior to assembly.

The invention will be better understood on reading the following description, given merely by way of example and with reference to the drawings, in which:

FIG. 1 is a perspective view of an injection device formed by a syringe 1 and a protection unit 2. The terms "proximal" and "rear" are used hereinafter as synonyms, as are the terms "distal" and "front".

The syringe 1 is a glass syringe of standard shape and intended for a single use. It contains a liquid to be injected, intramuscularly or subcutaneously, into a patient. It therefore comprises a body 4 and a needle 6 as may be seen, in particular, in FIG. 6. This needle is joined to the distal end of the body 4 by a ferrule 7.

The syringe further comprises a plunger 8 engaged in the body 4. This plunger conventionally comprises a rod 10 provided at its distal end with a plug 12, as may be seen in FIG. 6, and with a support head 14 on which the thumb of the practitioner's hand is intended to rest.

Figure 6:
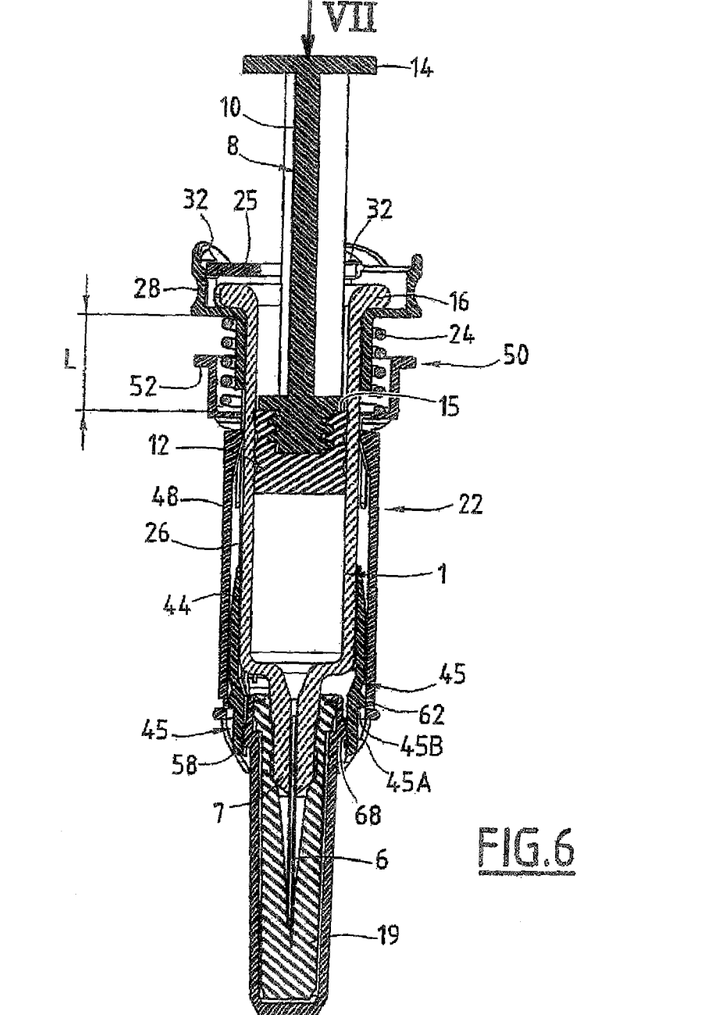
FIG. 6 is a view, along the same sectional plane as in FIG. 5, of the injection device according to the invention prior to use.

The rod 10 has, in its common portion, a section smaller than that of the plug 12, thus forming a peripheral shoulder 15, as may be seen in FIG. 6, on the plug 12 around the rod 10.

The syringe body 4 comprises, in its proximal portion, a collar 16 circumferentially delimiting two diametrically opposed lugs 18 normally intended, in particular in the absence of the unit 2, to form support surfaces for the practitioner's index and middle fingers when handling the syringe and injecting the liquid located therein.

Initially, the needle 6 is protected by a movable cap 19 fixed to the body of the syringe by being engaged on the ferrule 7.

The protection unit 2, having a general axis X-X, basically comprises, as shown in FIG. 1:
a generally tubular support 20;
a protective sleeve 22 arranged coaxially with the support 20 and having a diameter greater than that of the support,
a spring 14; and
a clip 25 for stopping the plunger and for attaching the syringe to the protective unit.

Figure 2:
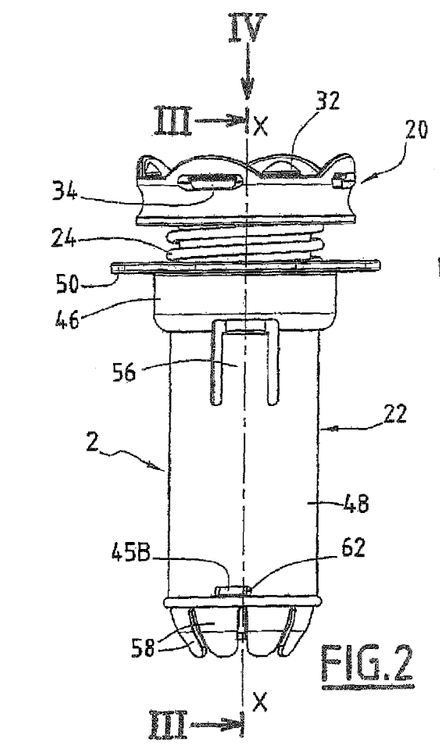
FIG. 2 is an elevation of the protection device pertaining to the injection device of FIG. 1, in the retracted position.

These elements will each be described in detail hereinafter with reference to FIG. 2 to 4.

The support 20 comprises a substantially cylindrical main portion 26 having an internal diameter substantially equal to the external diameter of the syringe body 4. This portion 26 has two diametrically opposed longitudinal recesses 26A. The portion 26 is extended, at is proximal end, by a secondary portion 28 having greater internal and external diameters than those of the main portion 26, forming a radial shoulder 29. The portion 28 has an internal diameter greater than the maximum diameter of the syringe collar 16.

The proximal portion 28 is provided with means 30 for fixing the clip 25 so that said clip surrounds the syringe collar 16 between the shoulder 29 and the clip 25, as shown in FIG. 6.

Figure 4:
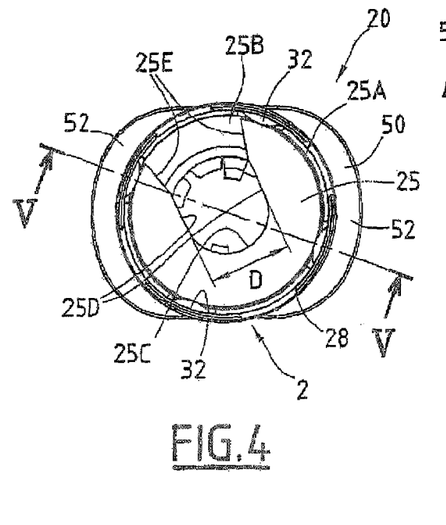
FIG. 4 is a plan view in the direction of arrow IV indicated in FIG. 2.

The clip 25, as may be seen in FIG. 4, is planar and is in the shape of a hollowed disc so as to form a U. It is delimited at its periphery by a circular contour 25A, the diameter of which is very slightly smaller than the internal diameter of the secondary portion 28. It has a notch 25B engaging in the disc forming the clip beyond the centre thereof. This notch 25B opens radially at the periphery of the disc forming the clip. It has a semi-circular base 25C and two parallel lips 25D extending the base 25C. These lips 25D are extended, up to the periphery 25A of the disc, by divergent faces 25E, so the notch 25B flares in the vicinity of its opening end.

The diameter of the base 25C and the distance separating the lips 25D, both designated by D, are chosen to be greater than the diameter of the common portion of the plunger rod 10 and smaller than the diameter of the plug 12 extending the rod 10. This diameter D is thus smaller than the internal section of the syringe body 4.

The fixing means 30 comprise diametrically opposed deformable hooks 32 which are carried by the portion 28 of the protector support. These hooks may be seen, in particular, in FIGS. 1 and 5. The distance separating the diametrically opposed hooks is smaller than the external diameter of the clip 25. Orifices 34 are formed in the portion 28 along the hooks 32 to impart resilience to said hooks.

Each of these hooks forms a substantially truncated cone-shaped ramp 32A flaring toward the free end of the portion 28. These ramps 32A are intended to allow the hooks to be pushed resiliently outward under the effect of the clip 25 when the support 20 is fixed to the syringe 1. The hooks 32 are set apart from the shoulder 29 by a distance substantially equal to the cumulative thicknesses of the lugs 18 and the clip 25. The hooks 32 thus form a clip-on engagement means for the clip 25 for fixing the syringe collar 16.

Two cruciform through-grooves 36 are formed, one facing the other, in the main portion 26. Each groove consists of a first rectilinear portion 38, extending substantially along the axis X-X of the support 20 over a length greater than that of the needle 6, and of a second rectilinear portion 40, extending in an inclined manner relative to the same axis X-X. The inclined portion 40 opens at the proximal end of the first rectilinear portion 38, forming a V, the point of which is directed away from the proximal side of the unit 2.

Figure 5:
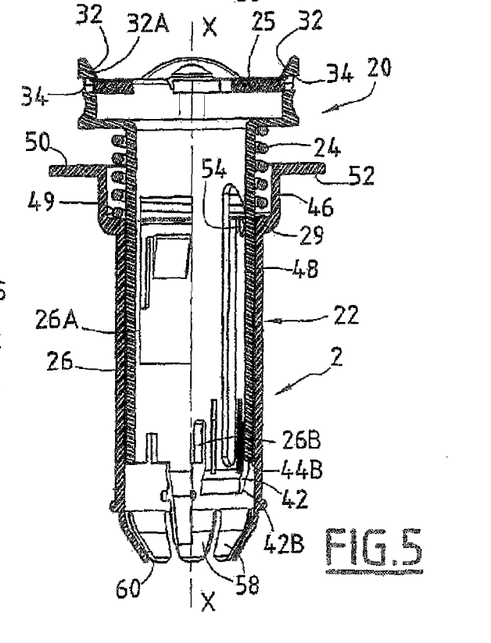
FIG. 5 is a cross-section along the plane V-V indicated in FIG. 4.

The main portion 26 comprises, at its distal end, a pair of diametrically opposed resilient tongues 42, each located in the extension of the grooves 36 (FIG. 5). These tongues 42 have a substantially cylindrical inner face 42A and a substantially truncated cone-shaped outer face 42B diverging toward the rear.

The main portion 26 comprises a pair of diametrically opposed outer ramps 44 located between the resilient tongues along the circumference of the distal end of this portion. They have a substantially truncated cone-shaped inclined outer surface 44A, diverging toward the front, and a substantially planar distal surface 44B. The outer surfaces 44A are thus turned toward the recesses 26A.

The longitudinal recesses 26A are formed in the main portion 26 (FIG. 3) at the proximal end of these ramps 44.

Furthermore, either side of the tongues 42, axial slots 26B are provided from the distal end of the support so that, prior to insertion of the body 4 of the syringe 1 within the support 20, these tongues 42 are radially deformable, especially inwardly.

At its distal or front end, the main portion 26 has, between the resilient tongues 42, two further tongues 45 for axially joining the protector 22 and the protector support 20 in the presence of the protective cap 19 placed over the syringe body.

Figure 3:
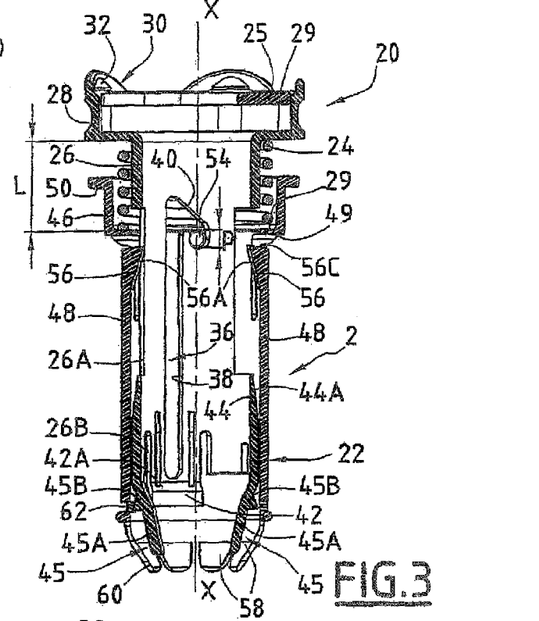
FIG. 3 is a cross-section along the plane III-III indicated in FIG. 2.

More specifically, and as shown in FIG. 3, these tongues each comprise a leg 45A extending the main portion 26 and integral therewith. Each leg 45A carries, on its outside, a projection 45B capable of engaging with a complementary orifice formed in the protector.

The projections 45B are provided over half of the length of the legs 45A, extending from the region at which the legs are connected to the main portion 26. The legs 45A thus extend beyond the projections 45B.

As shown in FIG. 3, the tongues are, in the rest state, inclined toward the axis X-X of the support, i.e. they converge toward one another in the direction of their free end and they extend in the extension of the inner passage delimited by the protector support.

These tongues 45 are outwardly resiliently deformable so that, in the rest position, the projections are contained entirely within the extension of the general bulk of the main portion 26 whereas, in the deformed position, the projections 45B extend radially outward beyond the extension of the general bulk of the main portion 26.

The distance separating the free ends of the two tongues 45, when they are in their rest position, is smaller than the minimum external diameter of the ring for fixing the protective syringe cap 19.

The length of the protective sleeve 22 is substantially equal to that of the syringe body 4. The sleeve consists of two cylindrical portions 46 and 48, the diameter of the proximal portion 46 being slightly greater than that of the main portion 48. These two portions connect to form a radial shoulder 49.

The sleeve 22 integrally comprises, in its proximal portion, an outer flange 50 in the form of two diametrically opposed lugs 52 (FIGS. 4 and 5).

Also in its proximal portion, but within the protective sleeve 22, two diametrically opposed studs 54 are integral with the sleeve (FIG. 5). These two studs are received and guided in the two grooves 36 in the support respectively. The support and the sleeve can thus be moved in translation relative to each other along the common axis thereof and in limited rotation about the same axis when the studs are in the inclined portions 40. The inclined portions 40 then form pockets for fixing the studs 54, these pockets having a fixing depth denoted by p in FIG. 3. This depth is measured along the axis of the protector.

Figure 13:
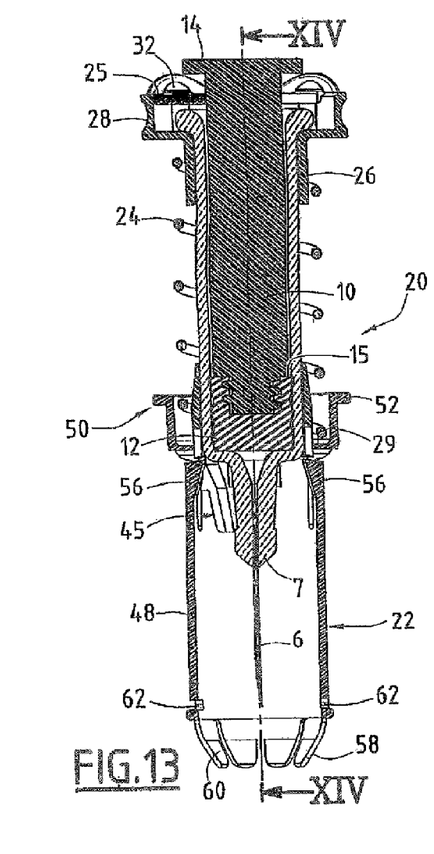
FIG. 13 to 15 show the injection device in the extended position, FIG. 13 being a view similar to that of FIG. 10, FIG. 14 being a cross-section along the plane XIV-XIV indicated in FIG. 13 and FIG. 15 being a view identical to that of FIG. 13, the syringe not being shown.
Figure 14:
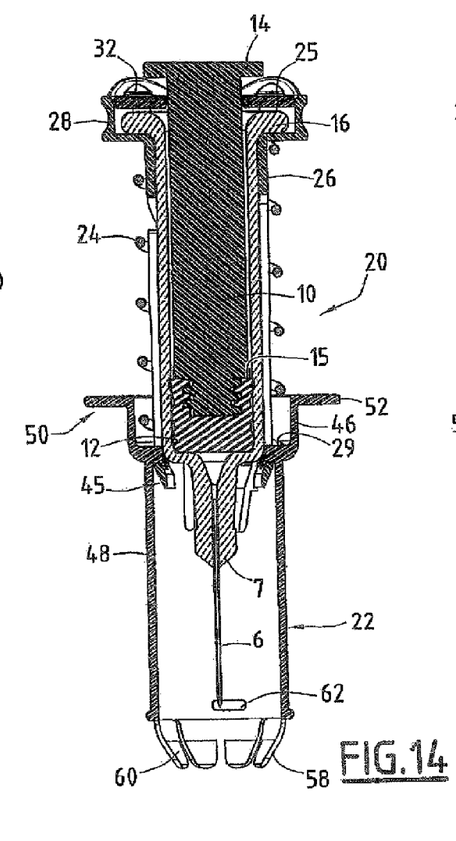
Figure 15:
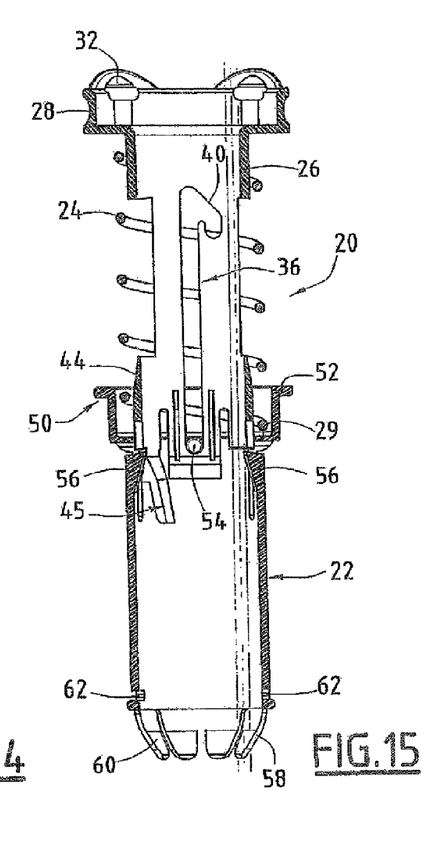

The support 20 and the sleeve 22 are movable between a retracted position of the sleeve, in which most of the sleeve covers most of the support and the studs 54 are located at the distal end of each of the inclined groove portions 40 as illustrated in FIG. 2 to 8, and an extended position of the sleeve, in which said sleeve projects axially from the support and the studs are located at the distal end of the rectilinear groove portion 38 as illustrated in FIG. 13 to 15.

When the syringe 1 is fixed to the unit 2, these end positions correspond respectively to an injection configuration in which the needle 6 of the syringe 1 is released and intended to be inserted into a patient and to a protective configuration in which this needle is surrounded by the protective sleeve 22.

The proximal portion of the sleeve 22 further comprises, on its inside, a pair of diametrically opposed deformable longitudinal hooks 56. These hooks are delimited in the sleeve 22 by lateral slots. Their distal end is connected to the sleeve. At its free proximal end, each hook has an inner protrusion.

In the absence of the syringe, and as shown in FIG. 3, the outer surfaces of the hooks 56 extend in the extension of the sleeve. The inner protrusions of these hooks, on the other hand, project inside the cylindrical passage delimited by the sleeve 22. Each protrusion has a substantially truncated cone-shaped front face 56A extending toward the front of the axis of the sleeve 22. These front faces 56A are thus turned toward the front end of the protector.

Each front face 56A is adapted to cooperate with an inclined surface 44A formed by the ramps 44 of the support.

At its free end, each hook 56 has an inclined transverse front 56C forming a stop.

In the retracted position of the sleeve, the hooks 56 extend inside recesses 26A formed in the support 20. In the extended position of the sleeve, as shown in FIG. 13, the end faces 56C of the hooks 56 axially abut the tongues 42, the hooks and tongues thus forming a rigid locking unit in the extended position.

The sleeve 22 is further provided, at the distal end thereof, with a crown of deformable tongues 58, the distal edges of which form a substantially circular opening 60, the diameter of which is smaller than the internal diameter of the main portion 26 of the support 20.

Finally, at it distal end, the main portion 48 of the protective sleeve comprises two oblong through-orifices 62 capable of receiving the projections 45B carried by the second pair of tongues 45 when these tongues are deformed under the effect of the ring of the needle protection cap 19 engaged on a syringe contained in the device.

In the absence of a cap, i.e. when the tongues 45 are in their rest position, the projections 45B are entirely outside the orifices 62, allowing free displacement of the protector relative to the support.

The spring 24 is a spiral spring arranged between the protective sleeve 22 and the protector support 20. More specifically, the spring is accommodated between the shoulder 29 of the support 20 and the shoulder 49 of the sleeve 22.

In the retracted position of the sleeve, the spring 24 is in a compressed state, thus having decompression energy associated with the rigidity of the spring and with the difference between the length of the spring in the rest state and the length thereof, denoted by L in FIG. 2 to 8, in the compressed state. In other words, the spring 24 has an additional compressive force threshold corresponding to the minimum force required further to compress the spring from its initial compressed state as shown in FIG. 2 to 8. The stiffness of the spring and/or the initial compression length L are chosen so that this force threshold is greater than the thrust required to displace the plunger 8 of the syringe 1 throughout the injection stroke thereof. More specifically, the force of the spring in the locked state is greater than the sum of the injection force, i.e. the force for discharging the liquid out of the needle 6 of the syringe 1, and the stresses for the detachment and sliding of the pusher 12 within the syringe body 4.

The cap 19 is generally tubular in shape and is shown in FIGS. 1 and 6.

It is adapted to surround the needle 6 prior to use of the syringe 1. This cap is closed at one of its ends and its opposing end is formed by an annular ring 68, the external diameter of which is suitable both for being joined to the surface 42A of the tongues 42 and for being greater than the diameter of the opening 60 formed by the tongues 58 of the protective sleeve 22. The inner face of this ring 68 is intended to adhere to the glass ferrule 7 of the syringe body where the needle 6 is fixed, in particular for ensuring a degree of imperviousness to bacteria.

Furthermore, the external diameter of the ring 68 of the cap is greater than the distance separating the free ends of the tongues 45, in the rest state.

The injection device according to the invention operates as follows.

The protection device 2 is assembled in its retracted configuration, i.e. that of FIG. 2 to 8. For this purpose, the protective sleeve 22 is slipped around the support 20 from the distal end of the support, providing the spring 24 therebetween. More specifically, the sleeve 22 is axially displaced toward the rear relative to the support, while at the same time outwardly radially deforming the hooks 56 using a suitable tool, at least until they axially reach the front portion of the longitudinal recesses 26A.

Then, while still displacing the sleeve toward the rear, the studs 54 are applied against the outer surfaces 42B of the tongues 42, inwardly deforming said tongues until the pegs are received in the rectilinear portions 38. The protector 22 is then displaced toward the rear until the studs 54 are received in the inclined groove portions 40 by causing the support and the protector to pivot relative to each other. The protector is thus in the retracted position.

The glass syringe 1 is pre-filled with a liquid to be injected into a patient. This syringe is equipped with the cap 19 which surrounds the ferrule 9 of the syringe body 4.

Figure 7:
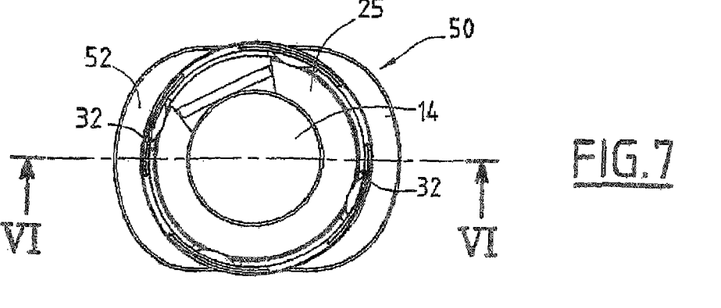
FIG. 7 is a plan view in the direction of arrow VII indicated in FIG. 6.

The syringe equipped with the cap 19 is inserted inside the unit 2 to form the injection device as shown in FIGS. 6 and 7. More specifically, the body 4 of the syringe is displaced substantially axially within the support 20.

The syringe body is displaced in the protector until the syringe collar 16 rests against the shoulder 29.

In this position, the clip 25 is then attached to the collar 16. For this purpose, if the plunger rod 10 is already mounted on the plug 12, the clip 25 is engaged around the plunger rod, the plunger rod being in the notch. The clip 25 is displaced along the length of the rod 10, then engaged with the main portion 28, thus radially outwardly deforming the hooks 32 so as resiliently to interlock the clip.

The lugs 18 of the syringe collar 16 are then fixed axially by the clip 25, itself fixed by the hooks 32.

If the syringe collar 16 is entirely clipped on inside the portion 28, it can no longer fulfil its conventional role of forming a support surface for the practitioner's index and middle fingers. This support function is performed by the flange 50 which is integral with the sleeve 22. If the length of the protective sleeve 22 is substantially equal to that of the syringe body 4 and/or the flange 50 is provided in the region of the proximal end of this sleeve, the practitioner can then handle the syringe by resting his thumb on the support head 14 of the plunger 8, and by resting his index and middle fingers on the faces of the lugs 52 directed toward the needle 6.

Moreover, if the syringe 1 is fixed to the protector support 20 as shown in FIGS. 6 and 7, the cap 19 projects outside the protective sleeve 22.

Furthermore, the widened external diameter of the ring 68 of the cap is engaged between the free ends of the tongues 45, thus radially outwardly deforming them. Under the effect of this deformation, the projections 45B are received in the orifices 62. In this position, the cooperation of the projections 45B, carried by the protector support, and the orifices 62 formed in the protector axially joins the protector and the support, thus preventing release of the spring, the stud 54 being unable to leave the end of the cross with which it is engaged.

When the practitioner is ready to inject the liquid contained in the syringe, he withdraws the cap 19 by pulling it axially forward.

To withdraw the cap, the practitioner can hold the syringe, fixing the protector from the support surfaces 50 with one hand, and pull on the cap 19 with the other hand. Even if there is a very high degree of resistance to the withdrawal of the cap, the positive axial connection provided by the projections 45B, which are engaged in the orifices 62, prevents the spring 24 from being able to be compressed and the studs 54 from being able to be released outside the fixing cross.

There is therefore no risk of the needle protector being accidentally released when the cap is withdrawn.

On the other hand, after withdrawal of the cap as shown in FIG. 7, the protector 22 can be displaced relative to the support 20, since the tongues 45 resume their rest position under the effect of the resilience thereof and the projections 45A are then released from the orifices 62.

After the detachment of the ring 68 from the ferrule 9, the ring 68 passes through the opening 60 by deforming the tongues 58. Once the cap 19 has been withdrawn, the tongues 58 resume their initial position.

The practitioner may then have cause to carry out an operation known as a "vein test". This consists in checking that the syringe has been injected correctly into a patient's muscle and not into an artery or a vein. For this purpose, the plunger 8 is pulled toward the proximal end. If blood is drawn into the syringe body, the practitioner will deduce that the needle has been injected into a vein or an artery and will then start again to position the needle.

Figure 9:
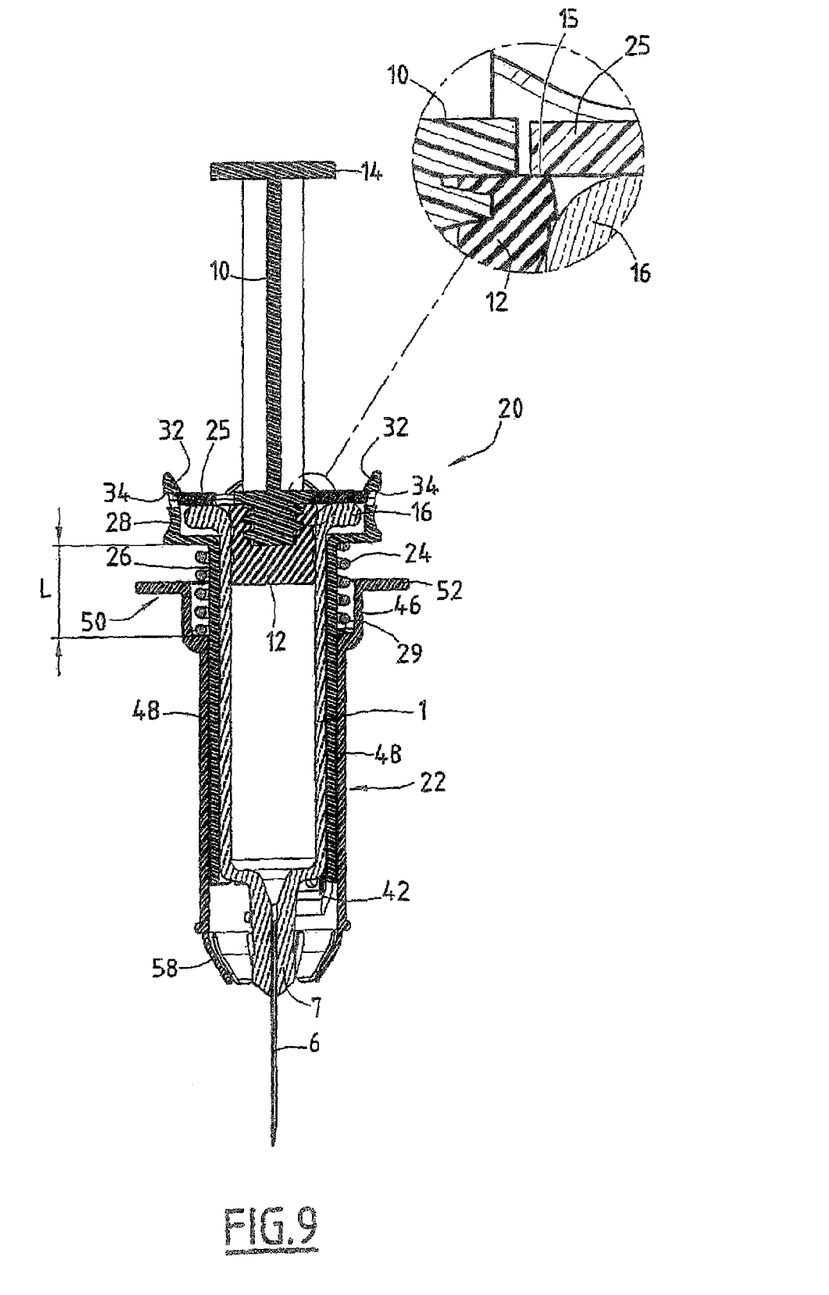
FIG. 9 is an identical view to that of FIG. 8, the plunger of the injection device being withdrawn into the end position.

In the event of an excessive pull being exerted by the practitioner onto the plunger rod, the plug 12 is halted in its displacement by abutting, via the shoulder 15, the clip 25 as illustrated in FIG. 9. The notch 25B defines a passage, the section of which is smaller than the section of the plug 12, thus preventing the plug from passing beyond the clip. The plunger rod 10, on the other hand, which has a smaller diameter, is able to slide freely through the notch 25B.

It will thus be understood that the clip 25 both fixes the syringe body 4 in the protector and forms a stop for stopping the plug 12 in the event of an excessive pull being exerted thereon. If the clip were not there, the plug could be extracted from the syringe body, thus rendering the injection device unusable.

The stopping of the plunger in the event of an excessive pull being exerted thereon is also useful during filling of the syringe through the needle, for example during take-up of lyophilisate.

Figure 8:
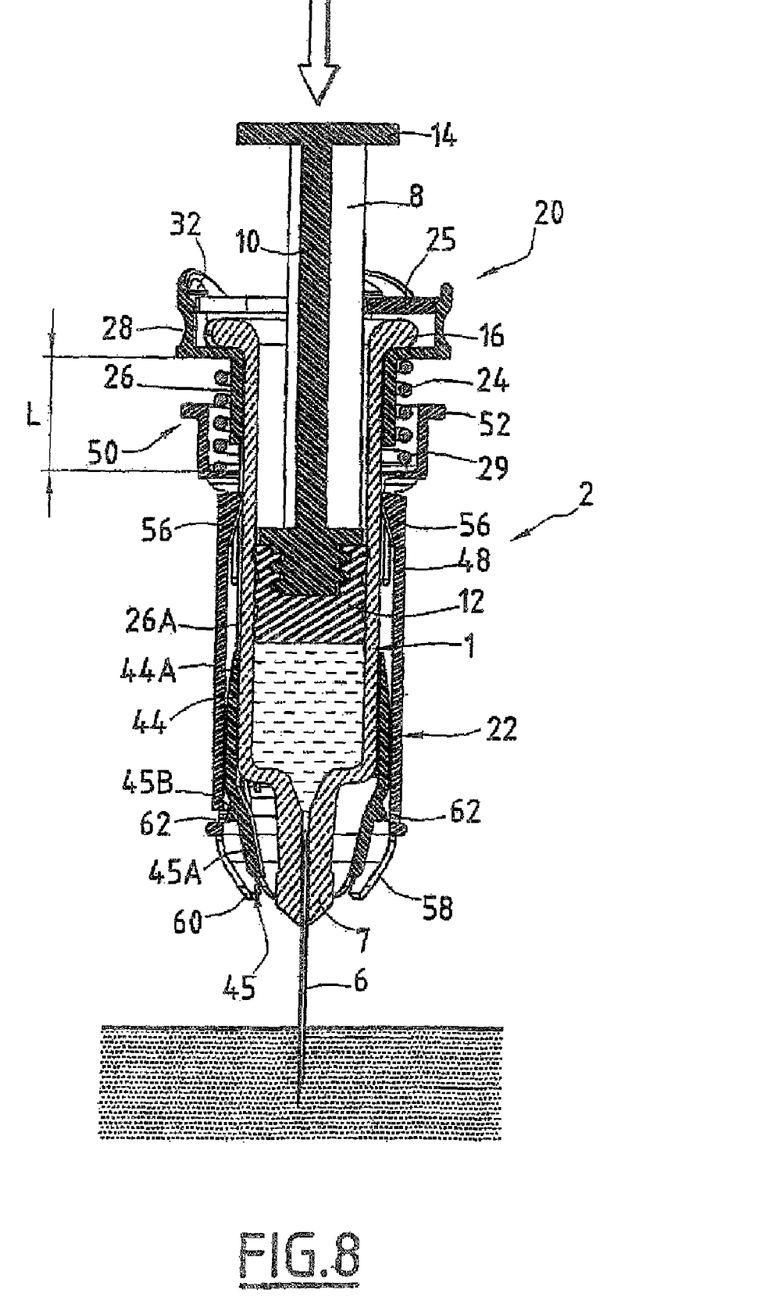
FIG. 8 is a view similar to that of FIG. 6, the injection device being ready for use.

In order to commence the injection process itself, the practitioner expels the liquid contained in the syringe by exerting a pushing force onto the support head 14 of the plunger, his index and middle fingers remaining in contact with the faces directed toward the needle of the lugs 52. During the injection there is no movement between the protector support 20 and the protective sleeve 22, the spring 24 remaining compressed at a length L as shown in FIG. 8.

The injection process is continued until the pusher 12 of the plunger 8 reaches the end of the injection stroke.

Figure 10:
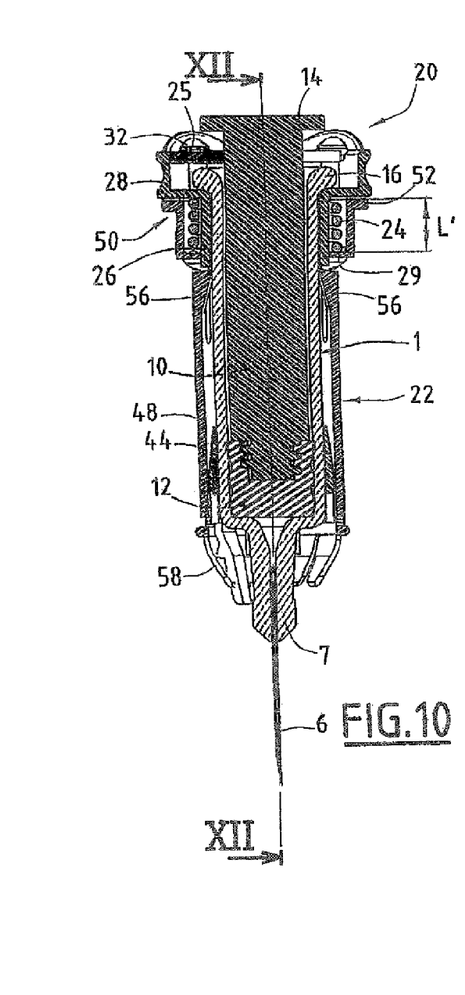
FIG. 10 is a view, along the same sectional plane as in FIG. 3, of the injection device at the end of use.
Figure 11:
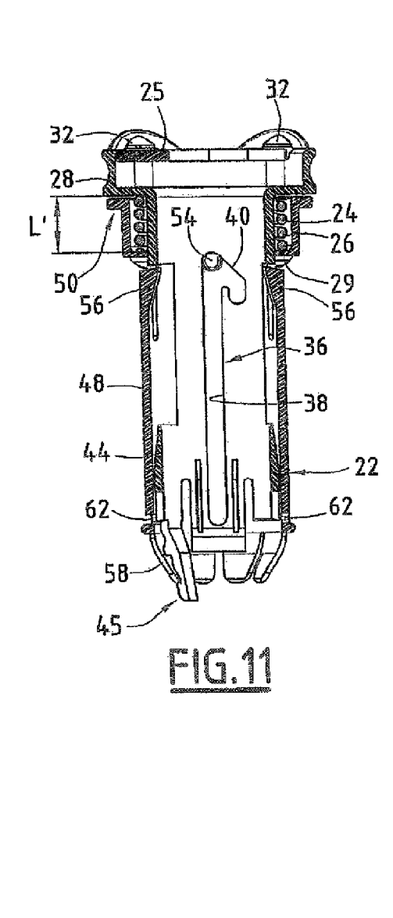
FIG. 11 is a view identical to that of FIG. 10, the syringe of the injection device not being shown.
Figure 12:
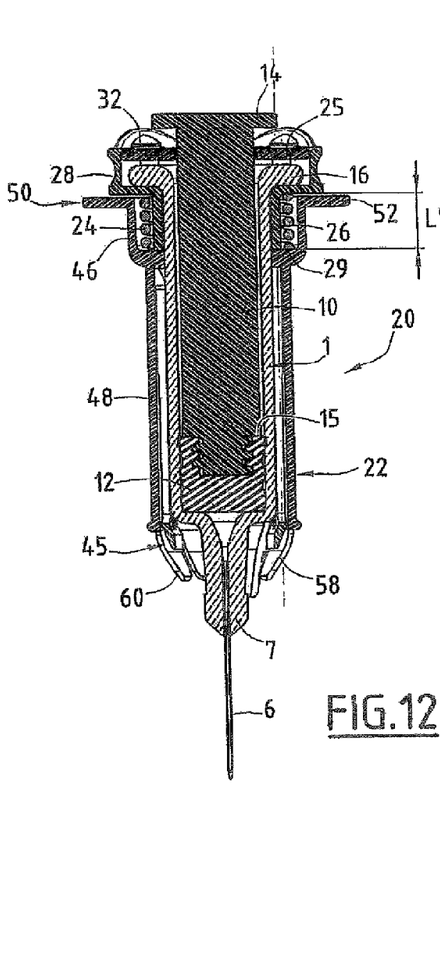
FIG. 12 is a cross-section along the plane XII-XII indicated in FIG. 10.

The practitioner then withdraws the needle from the patient. To release the protective unit 2, the practitioner subjects the plunger rod 8 to additional pressure. This pressure must be greater than the predetermined force produced by the spring 24 in the locked state, so that the spring is more compressed and passes from its length L to a shorter length L' as shown in FIG. 10 to 12. In order to do this, assuming a fixed syringe, the protective sleeve 22 is displaced axially toward the proximal end of the support 20. The practitioner performs this movement by exerting a corresponding pressure, using his index and middle fingers, on the lugs 52 of the flange 50 of the sleeve 22. This pressure, in combination with the translatory movement, causes the protective sleeve 22 to rotate about the syringe support 20, the studs 54 being guided by the inclined groove portions 40. This rotational movement continues until the studs reach the proximal end of this groove portion 40, i.e. the proximal end of the longitudinal groove portion 38, as may be seen in FIG. 11. The device 2 is then in the position for unlocking the spring 24.

The practitioner then releases the pressure previously exerted on the flange 50, allowing the spring 24 to relax into a rest state. The studs 54 are displaced in translation within the longitudinal groove portion 38, up to the distal end thereof, as shown in FIG. 13 to 15. The practitioner is able to control the translational movement of the protective sleeve 22 relative to the support 20 by gradually releasing his grip on the flange 50. Once the studs 54 have reached the distal end of the groove 36 (FIG. 15), the protector is in its extended position.

Furthermore, when the protective sleeve 22 is undergoing translational movement relative to the support 20, the hooks 56 lend support to the longitudinal recesses 26A until they slide along the distal ends 44 of the support by cooperation of their complementary surfaces 56A and 44A.

In the extended position of the protector, the hooks 56 are held by cooperation of the surfaces 56C and 44B, thus preventing the protector sleeve 22 from being brought into its initial position. Similarly, the sleeve 22 cannot easily be torn from the support 20, since the studs 54 abut the distal base of the longitudinal groove portion 38 (FIG. 15), the tongues 42 forming this base being radially held between the body of the syringe 1 and the protective sleeve 22.

The injection device according to the invention is thus easy to use while allowing the practitioner to control the movement of the protective sleeve covering the needle. The number of parts of which the protective unit 2 shown consists is reduced to three.

The device according to the invention can be adapted to various types of syringe, with regard to both shape and volume. This device therefore has the advantage of not challenging the general shape of the syringes used and accordingly does not necessitate any modification of the industrial processes for filling these syringes.

Differing variations of the device according to the invention are conceivable:

- unlike the embodiment described hereinbefore, the studs 54 and/or the flange 50 of the protective sleeve 22 can be added to the sleeve 22 rather than being formed in one piece therewith;
- in contrast to the described device, the studs 54 can be provided over the outer surface of the protector support 20 and the guide groove 36 formed in the protective sleeve 22; and/or
- the support 20 can be formed in one piece with the syringe body 4.

The invention claimed is:

1. Needle protection device (2) comprising:
    a protector support (20) delimiting a conduit for receiving a syringe body (4);
    a needle protector (22) delimiting an end opening (60) for passage of a needle (6) and a needle protection cap (19) and having at its other end radial protuberances (50) forming a finger rest, which needle protector (22) is movable relative to the protector support (20) between a retracted position and an extended position;
    a compression spring (24) applied between the protector support (20) and the needle protector (22); and
    means (38, 40, 50) for initial fixing of the needle protector (22) counter to action of the compression spring (24), which means (38, 40, 50) are releasable by displacement of the needle protector (22) relative to the protector support (20) in a releasing direction,
    characterized in that the device comprises mechanical means (45, 62) for locking the needle protector (22) relative to the protector support (20) in the releasing direction, which mechanical means are activated under action of the needle protection cap (19) engaged in the end opening (60) in the needle protector (22) by a cooperation of the mechanical means (45, 62) with the needle protection cap (19), and the mechanical means (45, 62) are deactivatable by releasing the needle protection cap (19) outside the end opening (60) in the needle protector (22).

2. Needle protection device (2) according to claim 1, characterized in that the mechanical means comprise at least a resiliently deformable tongue (45) integral with one of the protector (22) and the support (20), each tongue (45) being displaceable between a locking position, in axial abutment against the other of the protector (22) and the support (20) in a presence of the cap (19), and an unlocking position, remote from the other of the protector (22) and the support (20) in an absence of the cap (19), each tongue (45) extending, while at rest, into its unlocking position, and in that each tongue (45) has an actuating range (45A) for deformed holding thereof in the locking position under the action of the cap (19) engaged in the end opening (60) in the needle protector (22).

3. Needle protection device (2) according to claim 2, characterized in that each tongue (45) has a projection (45B) capable of engaging with an orifice (62) formed in the other of the protector (22) and the support (20).

4. Needle protection device (2) according to claim 1, characterized in that the mechanical means comprise at least a resiliently deformable tongue (45) integral with the support (20), each tongue (45) being displaceable between a locking position, in axial abutment against the protector (22) in a presence of the cap (19), and an unlocking position, remote from the protector (22) in an absence of the cap (19), each tongue (45) extending, while at rest, into its unlocking position, and in that each tongue (45) has an actuating range (45A) for deformed holding thereof in the locking position under the action of the cap (19) engaged in the end opening (60) in the needle protector (22).

5. Needle protection device (2) according to claim 4, characterized in that each tongue (45) extends in an extension of the protector support (20) at a front end thereof.

6. Injection device comprising, on the one hand, a syringe (1) comprising a tubular body (4), to a distal end of which a needle (6) is fixed, and an injection piston (8) mounted to slide in the body (4) and, on the other hand, the needle protection device (2) according to claim 1.

* * * * *